(12) United States Patent
Allersma et al.

(10) Patent No.: US 11,692,201 B2
(45) Date of Patent: Jul. 4, 2023

(54) PEPPER PLANTS WITH IMPROVED PEST RESISTANCE

(71) Applicant: Seminis Vegetable Seeds, Inc., St. Louis, MO (US)

(72) Inventors: Anton Pieter Allersma, Berkel en Rodenrijs (NL); Diane Kerr Avner, Vacaville, CA (US); Terry Berke, Zamora, CA (US); Jonathan Tyler Eckard, Richmond, CA (US); Brian J. Just, Fort Myers, FL (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 17/933,715

(22) Filed: Sep. 20, 2022

(65) Prior Publication Data

US 2023/0144998 A1   May 11, 2023

Related U.S. Application Data

(62) Division of application No. 16/606,648, filed as application No. PCT/US2018/029178 on Apr. 24, 2018, now Pat. No. 11,479,789.

(60) Provisional application No. 62/490,554, filed on Apr. 26, 2017.

(51) Int. Cl.
| | | |
|---|---|---|
| *A01H 1/00* | (2006.01) | |
| *A01H 6/82* | (2018.01) | |
| *A01H 1/04* | (2006.01) | |
| *A01H 5/08* | (2018.01) | |
| *C12N 15/82* | (2006.01) | |
| *C12Q 1/6895* | (2018.01) | |

(52) U.S. Cl.
CPC ........... *A01H 1/1265* (2021.01); *A01H 1/045* (2021.01); *A01H 5/08* (2013.01); *A01H 6/822* (2018.05); *C12N 15/8285* (2013.01); *C12Q 1/6895* (2013.01); *C12Q 2600/13* (2013.01); *C12Q 2600/156* (2013.01)

(58) Field of Classification Search
CPC .................................................... A01H 1/1265
See application file for complete search history.

(56) References Cited

U.S. PATENT DOCUMENTS 8,524,991 B2 * 9/2013 Berke ..................... A01H 5/08
                                                              800/278
10,244,891 B2   4/2019 Fukunaga et al.

OTHER PUBLICATIONS

Barbary et al., "Plant Genetic Background Increasing the Efficiency and Durability of Major Resistance Genes to Root-knot Nematodes Can be Resolved into a Few Resistance QTLs," Front Plant Sci., 2016, 1-9, 7(632).

Barbary et al., "The plant genetic background affects the efficiency of the pepper major nematode resistance genes Me1 and Me3," Theor Appl Genet, 2014, 499-507, 127(499).

Celik et al., "Physical mapping of NBS-coding resistance genes to the Me-gene cluster on chromosome P9 reveals markers tightly linked to the N gene for root-knot nematode resistance in pepper," Mol. Breeding, vol. 36, No. 137, pp. 1-7; 2016.

Changkwian et al., "Fine mapping of the Me7 gene controlling resistance to Root-Knot Nematode (Meloidogyne incognita) in chili pepper," Retrieved from the internet: s-space.snu.ac.kr/bitstream/10371/117452/1/2016%20EUCAPIA%20%28%eb%aa%a8%eb%a5%b8%2c%ec%9d%b4%ec%a2%85%ed%98%b8%29.pdf; 2016.

Chen et al., "CaMi, a root-knot nematode resistance gene from hot pepper (*Capsium annuum* L.) confers nematode resistance in tomato," Cell Reports, vol. 26, No. 7, pp. 895-905; 2007.

Djian-Caporalino et al. "Root-knot nematode (*Meloidogyne* spp.) Me resistance genes in pepper (*Capsicum annuum* L.) are clustered on the P9 chromosome," Theor. Appl. Genet., vol. 114, No. 3; pp. 473-486; 2007.

Fazari et al., "The root-knot nematode resistance N-gene co-localizes in the Me-genes cluster on the pepper (*Capsicum annuum* L.) P9 chromosome," Plant Breeding, 2012, 665-673, 131.

Genbank AC238398, Retrieved from the internet: .ncbi.nln.nih.gov/nuccore/259014128/>nucleotides 91437-91810; 2009.

Genbank JW074370, Retrieved from the internet: .ncbi.nln.nih.gov/nuccore/JW074370/>nucleotides 1295-1007; 2012.

Goncalves et al., "Resistance to root-knot nematode (*Meloidogyne enterolobii*) in *Capsicum* spp. Accessions," Agrária—Revista Brasileira de Ciências Agrárias, 2014, 49-52, 9(1).

International Search Report for PCT/US18/029178, dated Aug. 31, 2018.

International Written Opinion for PCT/US18/029178, dated Aug. 31, 2018.

Invitation to Pay Additional Fees for PCT/US18/029178, dated Jul. 5, 2018.

Pegard, et al., Histological Characterization of Resistance to Different Root-Knot Nematode Species Related to Phenolics Accumulation in Capsicum annuum. Phytopathology, 2005, 95(2): 158-165.

(Continued)

*Primary Examiner* — David H Kruse
(74) *Attorney, Agent, or Firm* — Dentons US LLP; Alissa Eagle

(57) ABSTRACT

Pepper plants exhibiting resistance to root knot nematode species are provided, together with methods of producing, identifying, or selecting plants or germplasm with a root knot nematode resistance phenotype. Such plants include pepper plants comprising introgressed genomic regions conferring pest resistance. Compositions, including novel polymorphic markers for detecting plants comprising introgressed pest resistance alleles, are further provided.

21 Claims, 5 Drawing Sheets

Specification includes a Sequence Listing.

(56) References Cited

OTHER PUBLICATIONS

Uncu et al., "Development of a SNP-based CAPS assay for the Me1 gene conferring resistance to root knot nematode in pepper," Euphytica, vol. 206, No. 2, pp. 393-399; 2015.
"Yolo Wonder Sweet Pepper." Mlgardener, Aug. 26, 2021, migardener.com/store/seeds-by-category/all-seeds/peppers/yolo-wonder-sweet-pepper/#:-:text=The%20Yolo%20wonder%20pepper%20was,will%20produce%2Onnore%20than%20enough! (Year: 2021).

\* cited by examiner

Figure 4

| Haplotype Group | # of RILs in group | Marker_1 100.4 | Marker_2 103.29 | Marker_3 105.41 | Marker_4 105.82 | Marker_5 109.87 | Marker_6 109.87 | Marker_7 111.28 | Marker_8 111.91 | Marker_9 111.91 | Marker_10 114.68 | Marker_11 116.71 | Marker_12 117.01 | Marker_13 122.07 | Haplotype LS Means |
|---|---|---|---|---|---|---|---|---|---|---|---|---|---|---|---|
| 1 | 56 | A | A | A | A | A | A | A | A | A | A | A | A | A | 37.151 |
| 2 | 6 | A | A | A | A | A | A | A | A | A | A | A | A | B | 33.968 |
| 3 | 1 | A | A | A | A | A | A | A | A | A | A | B | B | B | 26.767 |
| 4 | 3 | A | A | A | A | A | A | A | A | A | B | B | B | B | 57.428 |
| 5 | 4 | A | A | A | A | B | B | B | B | B | B | B | B | B | 80.221 |
| 6 | 3 | A | A | B | B | B | B | B | B | B | B | B | B | B | 82.283 |
| 7 | 3 | A | B | B | B | B | B | B | B | B | B | B | B | B | 82.956 |
| 8 | 58 | B | B | B | B | B | B | B | B | B | B | B | B | B | 93.172 |
| 9 | 1 | B | B | B | B | B | B | B | B | B | B | B | B | A | 68.025 |
| 10 | 2 | B | B | B | B | B | B | B | B | B | B | A | A | A | 83.900 |
| 11 | 1 | B | B | B | B | B | B | B | B | B | A | A | A | A | 105.358 |
| 12 | 2 | B | B | B | B | B | B | A | A | A | A | A | A | A | 39.826 |
| 13 | 2 | B | B | B | B | A | A | A | A | A | A | A | A | A | 37.728 |
| 14 | 1 | B | A | A | A | A | A | A | A | A | A | A | A | A | 28.267 |

SEQUENCE LISTING

```
Sequence total quantity: 25
SEQ ID NO: 1              moltype = DNA  length = 480
FEATURE                   Location/Qualifiers
source                    1..480
                          mol_type = genomic DNA
                          organism = Capsicum annuum
SEQUENCE: 1
taaggaatac attaacacgt gtncgcatta taaatcatta ccagtcaaat tttaactcct   60
gtctnaacaa tataatagct cagaattcat tcaagtgctt atacatttaa matgtcgctg  120
catgcataag aattagcagt gacttagtag atgatagagc attcaacatg agttcccttc  180
aaaagaatat aaaagaacta ttagtttgag agtttatgga agtcaccata cctgaagaat  240
gtctcaatcc cttgacagca tcaaaattct tgtaggtata gccaacaaaa cttaaatctt  300
caggaataag gcgcttctgc aaaaaaaaat tacaacaaaa aagatttatt taagcatgga  360
attagaagaa aaggtgttcc ggaaaagaga aatagaaaag taagctggag aagaaaattc  420
caaaaacgat gatagcaaga ctgctcagna aaacatggtt acattcagta gggatgtagg  480

SEQ ID NO: 2              moltype = DNA  length = 31
FEATURE                   Location/Qualifiers
source                    1..31
                          mol_type = other DNA
                          organism = synthetic construct
SEQUENCE: 2
atcattacca gtcaaatttt aactcctgtc t                                  31

SEQ ID NO: 3              moltype = DNA  length = 31
FEATURE                   Location/Qualifiers
source                    1..31
                          mol_type = other DNA
                          organism = synthetic construct
```

-continued

```
SEQUENCE: 3
tgttgaatgc tctatcatct actaagtcac t                                    31

SEQ ID NO: 4            moltype = DNA   length = 16
FEATURE                 Location/Qualifiers
source                  1..16
                        mol_type = other DNA
                        organism = synthetic construct
SEQUENCE: 4
cagcgacatg ttaaat                                                     16

SEQ ID NO: 5            moltype = DNA   length = 16
FEATURE                 Location/Qualifiers
source                  1..16
                        mol_type = other DNA
                        organism = synthetic construct
SEQUENCE: 5
cagcgacatt ttaaat                                                     16

SEQ ID NO: 6            moltype = DNA   length = 490
FEATURE                 Location/Qualifiers
source                  1..490
                        mol_type = genomic DNA
                        organism = Capsicum annuum
SEQUENCE: 6
agtaaatgtg aatgctacgg taagacgtca tggttaatag actcgtttgc caaatagagt     60
atgccttcaa ttacagtttt tttgtgcctg atattacata cggtagtaca tcatgaataa    120
tagatttgtw tgccaaatag agtatggctt caattacatg attttttgtga atgctaagat   180
aagacgtact ccttgtcaaa caaaatattc cttcaattac atgttttttg tgcttggtgt    240
tacatacggt agtacatcat gaataataga cttgtttgcc aaatagagta cgtcttcaat    300
tacatgcttt ttggcgaatg ctacggtaaa acgtcatgaa tagtttgcct cgattgctaa    360
atagaatatg ccttcaatta catgattttt tgtacttgtc gttgcctgtg gtaggacgtc    420
atggataatc gactcatttg tcaaatggag tatgccttca attacatgct tttctgtgca    480
tgttgttacc                                                           490

SEQ ID NO: 7            moltype = DNA   length = 30
FEATURE                 Location/Qualifiers
source                  1..30
                        mol_type = other DNA
                        organism = synthetic construct
SEQUENCE: 7
cctgatatta catacggtag tacatcatga                                      30

SEQ ID NO: 8            moltype = DNA   length = 28
FEATURE                 Location/Qualifiers
source                  1..28
                        mol_type = other DNA
                        organism = synthetic construct
SEQUENCE: 8
agtacgtctt atcttagcat tcacaaaa                                        28

SEQ ID NO: 9            moltype = DNA   length = 18
FEATURE                 Location/Qualifiers
source                  1..18
                        mol_type = other DNA
                        organism = synthetic construct
SEQUENCE: 9
ctatttggca tacaaatc                                                   18

SEQ ID NO: 10           moltype = DNA   length = 14
FEATURE                 Location/Qualifiers
source                  1..14
                        mol_type = other DNA
                        organism = synthetic construct
SEQUENCE: 10
ttggcaaaca aatc                                                       14

SEQ ID NO: 11           moltype = DNA   length = 301
FEATURE                 Location/Qualifiers
source                  1..301
                        mol_type = genomic DNA
                        organism = Capsicum annuum
SEQUENCE: 11
aattggcaat ggcttgaaaa aagcttcaac aactattggc tgtttgtttt ggcttttgca     60
tgttagtggc attgccattg atactattga agttgtagcc atttcttttg cctttttgnta   120
acaagaattg atcttaattt tcttggtata raagttaaag agtatggtgt tggtaatatg    180
atgtgatttt gtattgagag gataaagaan ggattttta tgagaggtgg aaaattgaaa     240
tttggagttt ggtacatatt gttttgtcct acatggctgg ttcttattgg ttatgttgga   300
t                                                                    301
```

```
SEQ ID NO: 12            moltype = DNA   length = 27
FEATURE                  Location/Qualifiers
source                   1..27
                         mol_type = other DNA
                         organism = synthetic construct
SEQUENCE: 12
agttgtagcc atttcttttg ccttttg                                        27

SEQ ID NO: 13            moltype = DNA   length = 31
FEATURE                  Location/Qualifiers
source                   1..31
                         mol_type = other DNA
                         organism = synthetic construct
SEQUENCE: 13
ttctttatcc tctcaataca aaatcacatc a                                   31

SEQ ID NO: 14            moltype = DNA   length = 23
FEATURE                  Location/Qualifiers
source                   1..23
                         mol_type = other DNA
                         organism = synthetic construct
SEQUENCE: 14
ccatactctt taacttttat acc                                            23

SEQ ID NO: 15            moltype = DNA   length = 23
FEATURE                  Location/Qualifiers
source                   1..23
                         mol_type = other DNA
                         organism = synthetic construct
SEQUENCE: 15
ccatactctt taacttctat acc                                            23

SEQ ID NO: 16            moltype = DNA   length = 301
FEATURE                  Location/Qualifiers
source                   1..301
                         mol_type = genomic DNA
                         organism = Capsicum annuum
SEQUENCE: 16
gaaggctgct acagaaatag ataattggca gccatgccct tgtgcaagta gtagtacagt     60
aataatgagc atcttgtctg gaacatagga ttacaagctt gggatattgt tctttcatt    120
cttgaatgag ggtactcttt gttacgagtg yggttcgcca cttttcttgta ttttctaatt  180
tnagtcaaga gtgattgtgt ctgttttaaa tgggattttta cttgtcacct tctacaataa  240
gattgtgtgg gtaggaaaaa taacctcctt cctgctattt ggtcaaaaat tgagatctgt   300
g                                                                   301

SEQ ID NO: 17            moltype = DNA   length = 29
FEATURE                  Location/Qualifiers
source                   1..29
                         mol_type = other DNA
                         organism = synthetic construct
SEQUENCE: 17
gcttgggata ttgttctttt cattcttga                                      29

SEQ ID NO: 18            moltype = DNA   length = 28
FEATURE                  Location/Qualifiers
source                   1..28
                         mol_type = other DNA
                         organism = synthetic construct
SEQUENCE: 18
tcccatttaa aacagacaca atcactct                                       28

SEQ ID NO: 19            moltype = DNA   length = 19
FEATURE                  Location/Qualifiers
source                   1..19
                         mol_type = other DNA
                         organism = synthetic construct
SEQUENCE: 19
ttgttacgag tgtggttcg                                                 19

SEQ ID NO: 20            moltype = DNA   length = 16
FEATURE                  Location/Qualifiers
source                   1..16
                         mol_type = other DNA
                         organism = synthetic construct
SEQUENCE: 20
ttacgagtgc ggttcg                                                    16
```

```
SEQ ID NO: 21          moltype = DNA  length = 301
FEATURE                Location/Qualifiers
source                 1..301
                       mol_type = genomic DNA
                       organism = Capsicum annuum
SEQUENCE: 21
agaatttcaa ctacttgact cataagaggc ctcccttttg ggttttggct aaggcattga    60
taggcaagac tagcaacctt tacgatgatt ttggaggagt actgtccttc gagtctaggg   120
tcgagtatct taaagagttt cttgtcatga stcaggagcg gacgtgccca ctctacaagg   180
ttgtattccc ggcttggcct agtcttgtcg attgctctcc ttccgatgag catctcaagc   240
aaaacaacac caaaagcata gacgtcgctt cttgctgtca aatgtcctga atgattcaac   300
t                                                                  301

SEQ ID NO: 22          moltype = DNA  length = 27
FEATURE                Location/Qualifiers
source                 1..27
                       mol_type = other DNA
                       organism = synthetic construct
SEQUENCE: 22
cgagtctagg gtcgagtatc ttaaaga                                       27

SEQ ID NO: 23          moltype = DNA  length = 21
FEATURE                Location/Qualifiers
source                 1..21
                       mol_type = other DNA
                       organism = synthetic construct
SEQUENCE: 23
aagccgggaa tacaaccttg t                                             21

SEQ ID NO: 24          moltype = DNA  length = 21
FEATURE                Location/Qualifiers
source                 1..21
                       mol_type = other DNA
                       organism = synthetic construct
SEQUENCE: 24
tttcttgtca tgagtcagga g                                             21

SEQ ID NO: 25          moltype = DNA  length = 20
FEATURE                Location/Qualifiers
source                 1..20
                       mol_type = other DNA
                       organism = synthetic construct
SEQUENCE: 25
ttcttgtcat gactcaggag                                               20
```

PEPPER PLANTS WITH IMPROVED PEST RESISTANCE

REFERENCE TO RELATED APPLICATION

This application is a divisional of U.S. patent application Ser. No. 16/606,648, filed Oct. 18, 2019, which is a 371 National Stage application of International Application No. PCT/US2018/029178, filed Apr. 24, 2018, which claims the benefit of U.S.

Provisional Application No. 62/490,554, filed Apr. 26, 2017, which are herein incorporated by reference in their entireties.

INCORPORATION OF SEQUENCE LISTING

A sequence listing containing the file named "SEMB025WO_ST26_Revised.xml" which is 24.3 kilobytes (measured in MS-Windows®) and created on Nov. 14, 2022, and comprises 25 sequences, and is incorporated herein by reference in its entirety.

FIELD OF THE INVENTION

The present invention relates to the field of plant breeding and more specifically to methods and compositions for producing pepper plants exhibiting improved pest resistance.

BACKGROUND

Pest resistance is an important trait in agriculture, particularly for the production of food crops. In pepper plants, root knot nematodes (RKN) result in significant yield loss and even plant death. Although RKN resistance alleles have been identified in pepper plants, known resistance alleles vary in their resistance against the different species of the RKN complex. Deployment of resistance loci starts an evolutionary arms race between pest and breeder leading to newly emerging species of RKN that are capable of reproducing on pepper plants carrying previously known forms of RKN resistance. Therefore, it is necessary that breeders find and develop new sources of RKN resistance with alternative resistance profiles and genetic variation to maintain good resistance levels and minimize crop loss in commercial pepper production.

SUMMARY

In one aspect, the invention provides a *Capsicum annuum* plant comprising an introgressed allele on chromosome 9 that confers increased resistance to root knot nematodes compared to a plant not comprising said allele, wherein said plant is a non-jalapeno variety, and wherein said introgressed allele is located between Marker_6 (SEQ ID NO: 1) and Marker 10 (SEQ ID NO: 21) on chromosome 9. In some embodiments, the plant is a variety selected from the group consisting of Anaheim, Ancho/Poblano, Asian Long Slim, Asian Short, Blocky or Bell, Capia, Cascabel, Cayenne, Chiltepins or Small Hots, Corno di Toro, Cubanelle, 'Fresno Chili', Hungarian Wax/Banana/Hungarian White, Ornamental, Pasilla, Pimiento, Santa Fe Grande, Serrano, and Waxy peppers. In certain embodiments, the plant has a blocky type fruit shape, a ¾ long type fruit shape, or a half long type fruit shape. For example, the fruit of the plant may have a length to width ratio less than 2.5:1, such as a length to width ratio of less than 2:1, or a length to width ratio of between 0.8 to 1.2.

In other embodiments, the *Capsicum annuum* plant comprises an introgressed allele flanked in the genome of said plant by position 250,338,645 bp and position 250,504,749 bp on chromosome 9 on the physical map of CM334 v1.55. The introgressed allele may be flanked in the genome of said plant by marker locus Marker_7 (SEQ ID NO: 6) and marker locus Marker_9 (SEQ ID NO: 16). In further embodiments, the *Capsicum annuum* plant comprises an introgressed allele comprising the resistance haplotype of HJA-114-1011. In certain embodiments, the introgressed allele has been introgressed from PX11435810, a sample of the seed of which has been deposited under ATCC Accession No. PTA-13408. In further embodiments, *Capsicum annuum* plant of the invention are resistant to isolates of the root knot nematode species *M. enterolobii, M. javanica, M. arenaria*, and *M. incognita*.

In another aspect, the invention provides a plant part of the *Capsicum annuum* plant of the invention, for example a cell, a seed, a root, a stem, a leaf, a fruit, a flower, or pollen.

In yet a further aspect, a method is provided for producing a *Capsicum annuum* plant exhibiting resistance to root knot nematodes, comprising: a) crossing a *Capsicum annuum* plant provided herein with itself or with a second *Capsicum annuum* plant of a different genotype to produce one or more progeny plants; and b) selecting a progeny plant comprising said introgressed allele. In certain embodiments, selecting said progeny plant comprises identifying a genetic marker genetically linked to said introgressed allele. In some embodiments, selecting said progeny plant comprises identifying a genetic marker within or genetically linked to a genomic region between 250,338,645 bp and 250,504,749 bp on chromosome 9 on the physical map of CM334 v1.55. Selecting said progeny may further comprise identifying a genetic marker within or genetically linked to a genomic region flanked in the genome of said plant by marker locus Marker_7 (SEQ ID NO: 6) and marker locus Marker_9 (SEQ ID NO: 16), for example detecting at least one polymorphism at a locus selected from the group consisting of marker locus Marker_7 (SEQ ID NO: 6), marker locus Marker_8 (SEQ ID NO: 11), and marker locus Marker_9 (SEQ ID NO: 16). The progeny plant may be an $F_2$-$F_6$ progeny plant, and the methods provided may comprises backcrossing, for example from 2-7 generations of backcrossing.

In another aspect, a method is provided for producing a *Capsicum annuum* plant exhibiting resistance to root knot nematodes, comprising introgressing into a plant a root knot nematode resistance allele, wherein said resistance allele is defined as located in a genomic region between 250,338,645 bp and 250,504,749 bp on chromosome 9 on the physical map of CM334 v1.55. In certain embodiments, said genomic region is flanked by Marker_7 (SEQ ID NO: 6) and marker locus Marker_9 (SEQ ID NO: 16). The method may comprise backcrossing, marker-assisted selection, or assaying for root knot nematode resistance.

In a further aspect, *Capsicum annuum* plant is provided that is obtainable by a method comprising the steps of: a) crossing a *Capsicum annuum* plant provided herein with itself or with a second *Capsicum annuum* plant of a different genotype to produce one or more progeny plants; and b) selecting a progeny plant comprising said introgressed allele. Selecting said progeny plant may comprise identifying a genetic marker genetically linked to said introgressed allele, for example identifying a genetic marker within or genetically linked to a genomic region flanked in the genome of said plant by marker locus Marker_7 (SEQ ID NO: 6) and marker locus Marker_9 (SEQ ID NO: 16). Selecting a progeny plant may further comprise detecting at least one polymorphism at a locus selected from the group consisting of marker locus Marker_7 (SEQ ID NO: 6), marker locus Marker_8 (SEQ ID NO: 11), and marker locus Marker_9 (SEQ ID NO: 16). In some embodiments, said progeny plant is an $F_2$-$F_6$ progeny plant. Producing said progeny plant may comprise backcrossing, for example from 2-7 generations of backcrossing.

In yet a further aspect, *Capsicum annuum* plant is provided that is obtainable by a method comprising the step of: introgressing into a plant a root knot nematode resistance allele, wherein said resistance allele is defined as located in a genomic region between 250,338,645 bp and 250,504,749 bp on chromosome 9 on the physical map of CM334 v1.55. In some embodiments, said genomic region is flanked by Marker_7 (SEQ ID NO: 6) and marker locus Marker_9 (SEQ ID NO: 16). In further embodiments, introgressing comprises backcrossing, marker-assisted selection, or assaying for said root knot nematode resistance.

In another aspect, methods are provided of selecting a *Capsicum annuum* plant exhibiting resistance to root knot nematodes, comprising: a) crossing a *Capsicum annuum* plant provided herein with itself or with a second *Capsicum annuum* plant of a different genotype to produce one or more progeny plants; and b) selecting a progeny plant comprising said introgressed allele. In certain embodiments, selecting said progeny plant comprises identifying a genetic marker genetically linked to said introgressed allele. Selecting said progeny plant may also comprise identifying a genetic marker within or genetically linked to a genomic region between 250,338,645 bp and 250,504,749 bp on chromosome 9 on the physical map of CM334 v1.55. In additional embodiments, said progeny plant comprises identifying a genetic marker within or genetically linked to a genomic region flanked in the genome of said plant by marker locus Marker_7 (SEQ ID NO: 6) and marker locus Marker_9 (SEQ ID NO: 16). Selecting a progeny plant may also comprise detecting at least one polymorphism at a locus selected from the group consisting of marker locus Marker_7 (SEQ ID NO: 6), marker locus Marker_8 (SEQ ID NO: 11), and marker locus Marker_9 (SEQ ID NO: 16). Said progeny plant may be an $F_2$-$F_6$ progeny plant. In some embodiments, producing said progeny plant comprises backcrossing, for example from 2-7 generations of backcrossing.

In a further aspect, methods are provided of producing a *Capsicum annuum* plant exhibiting resistance to root knot nematodes, comprising introgressing into a plant a root knot nematode resistance allele, wherein said resistance allele is defined as located in a genomic region between 250,338,645 bp and 250,504,749 bp on chromosome 9 on the physical map of CM334 v1.55. In certain embodiments, said genomic region is flanked by Marker_7 (SEQ ID NO: 6) and marker locus Marker_9 (SEQ ID NO: 16). Introgressing may comprise backcrossing, marker-assisted selection, or assaying for said root knot nematode resistance.

BRIEF DESCRIPTION OF THE DRAWINGS

FIG. 4: Fine mapping of the RKN resistance locus on chromosome 9. A genotype of "A" refers to a homozygous allele from HJA-114-1011 (Resistant parent) while "B" is homozygous for HJA-114-1096 (Sensitive parent). The Haplotype LSMeans represent the mean gallcount for each haplotype. A lower number indicates better resistance against *M. enterolobii*.

DETAILED DESCRIPTION

Figure 1:
FIG. 1: Fruit of jalapeno peppers are characterized by a typical bullet shape with a 2.5:1 length to width ratio. Fruit is generally harvested at the immature green stage.

Root knot nematodes (RKN) are microscopic roundworms of the genus *Meloidogyne* that parasitize the roots of a wide variety of crop plants, resulting in yield loss from infected fields. Several sources of RKN resistance are known in the field of pepper breeding. However, while these genes are known to provide some resistance to isolates of *M. javanica, M. incognita* or *M. arenaria*, the resistance against *M. enterolobii* for these sources is either unknown or not sufficiently robust. As resistance against *M. enterolobii* is becoming more important due to its aggressiveness and rapid emergence as a primary pest in important pepper growing regions of the world, such as Mexico and the US, new broad spectrum RKN resistance loci are needed.

The invention therefore provides novel RKN resistance loci on chromosome 9 of the *Capsicum annuum* genome that provides resistance to *M. icognita, M. arenaria* and *M. javanica* and to the emerging *M. enterolobii* species. Resistance genes that confer resistance to this emerging nematode species have not been previously described. Surprisingly, although the novel RKN resistance locus of the invention is located among known nematode resistance loci in pepper on chromosome 9, fine mapping of this novel locus demonstrates that it is distinct from and genetically unrelated to known sources of RKN resistance.

The invention additionally provides pepper plants comprising novel introgressions from donor lines that confer RKN resistance. Specifically, plants comprising the introgressed alleles described herein provide broad spectrum resistance to *M. icognita, M. arenaria, M. javanica*, and *M. enterolobii*. The invention therefore provides a chromosomal segment of approximately 4.8 cM located between approximately 109.87 cM and about 114.68 cM on the Monsanto linkage map of chromosome 9 that confers broad-spectrum resistance to RKN in pepper plants.

The invention further provides novel trait-linked markers that allow the accurate identification and tracking of the aforementioned chromosomal regions during plant breeding. In particular embodiments, the invention provides genetic markers within or genetically linked to a genomic region between about 109.87 cM and about 114.68 cM on chromosome 9. Other embodiments provide novel markers Marker_6 (SEQ ID NO: 1) comprising a SNP [C/A], Marker_7 (SEQ ID NO:6) comprising a SNP [T/A] at 250,504,749 bp of the public genome of CM334 v1.55, Marker_8 (SEQ ID NO:11) comprising a SNP [A/G] at 250,338,645 bp of the public genome CM334 v1.55, Marker_9 (SEQ ID NO:16) comprising a SNP [T/C] at 250,502,864 bp of the public genome CM334 v1.55, and Marker 10 (SEQ ID NO: 21) comprising a SNP [G/C] at 241,570,991 bp of the public genome CM334 v1.55, which are useful in detection and tracking of plants comprising RKN resistance. The official public genome of CM334 is publically available (Kim, et al. Nature Genetics 46, 270-278 (2014)), and can be accessed through the SOL genomics network.

I. Genomic Regions, Alleles, and Polymorphisms Associated with RKN Resistance in Pepper Plants RKN are soil-borne pests that infect plant roots, causing severe decreases in yield or even plant death. A broad range of crop plants is susceptible to RKN infection, leading to significant yield loss worldwide. Cultivar resistance is the most economically feasible way of controlling RKN infection due the high cost and variable performance of pesticide treatments. Intensive efforts have therefore been made to identify effective sources of RKN resistance. However, previously known introgressions from RKN resistant accessions confer resistance to only a subset of RKN species.

RKN species include, but are not limited to, *Meloidogyne acronea, Meloidogyne arenaria, Meloidogyne artiellia, Meloidogyne brevicauda, Meloidogyne chitwoodi, Meloidogyne coffeicola, Meloidogyne exigua, Meloidogyne fruglia, Meloidogyne gajuscus, Meloidogyne hapla, Meloidogyne incognita, Meloidogyne javanica, Meloidogyne* enterolobii (also known as *Meloidogyne mayaguensis*), *Meloidogyne naasi, Meloidogyne partityla*, and *Meloidogyne thamesi*. The *M. icognita, M. arenaria* and *M. javanica* and *M. enterolobii* species are of particular relevance as pests to commercial pepper plants.

Several sources of RKN resistance are known in the field of pepper breeding including CM334, PI322719 (also known as PM687), PI201234 (also known as PM217), and Carolina Cayenne. While the resistance profiles differ between these sources, previously known resistance genes have been mapped to a gene cluster at one end of chromosome 9. Of the known resistance genes, Me1 from PI201234, Me3 from PI322719 (likely the same as Me1 from CM334), and the N-gene from Carolina Cayenne are currently widely used in breeding programs. However, while these genes are known to provide some resistance to isolates of *M. javanica, M. incognita* or *M. arenaria*, the resistance against *M. enterolobii* is insufficient for those genes tested in the public. The newly identified resistance locus from HJA-114-1011 described herein provides resistance to *M. enterolobii, M. incognita, M. javanica*, and *M. arenaria*.

In certain embodiments, the invention therefore provides pepper plants comprising donor DNA from a RKN resistant line that maps between approximately 109.87 cM and about 114.68 cM on chromosome 9. This novel introgression provides resistance to RKN species including *M. enterolobii*. Genomic regions as described herein can be obtained from any wild or cultivated plant or line, including in certain embodiments pepper line PX11435810 (a sample of the seed of which has been deposited with the American Type Culture Collection (ATCC), 10801 University Boulevard, Manassas, Va. 20110-2209 USA under ATCC Accession No. PTA-13408, Dec. 12, 2012), which is a jalapeno hybrid having HJA-114-1011 as a parent and comprising the genomic regions as described herein. Plants provided herein include plants comprising the genetic source for the RKN resistance trait from pepper line PX11435810.

Other embodiments of the invention provide novel markers for the selection of the RKN resistance locus on chromosome 9 described herein. Examples of such markers include Marker_7, Marker_8, and Marker_9, which have been shown to be genetically linked to RKN resistance in plants.

II. Introgression of Genomic Regions Associated with RKN Resistance

Marker-assisted introgression involves the transfer of a chromosomal region defined by one or more markers from a first genetic background to a second. Offspring of a cross that contain the introgressed genomic region can be identified by the combination of markers characteristic of the desired introgressed genomic region from a first genetic background and both linked and unlinked markers characteristic of the second genetic background.

The present invention provides novel markers for identifying and tracking introgression of one or more of the genomic regions disclosed herein from an RKN resistant plant into a cultivated line. The invention further provides markers for identifying and tracking the novel introgressions disclosed herein during plant breeding, such as markers Marker_7, Marker_8, and Marker_9.

Markers within or linked to any of the genomic intervals of the present invention may be useful in a variety of breeding efforts that include introgression of genomic regions associated with pest resistance into a desired genetic background. For example, a marker within 40 cM, 20 cM, 15 cM, 10 cM, 5 cM, 2 cM, or 1 cM of a marker associated with pest resistance described herein can be used for marker-assisted introgression of genomic regions associated with a pest resistance phenotype.

Pepper plants comprising one or more introgressed regions associated with a desired phenotype wherein at least 10%, 25%, 50%, 75%, 90%, or 99% of the remaining genomic sequences carry markers whose alleles match the recurrent parent genotype outside of the region targeted for pest resistance introgression are also provided. Pepper plants comprising an introgressed region closely linked to, or adjacent to, the genomic regions and markers provided herein and associated with a pest resistance phenotype are also provided.

III. Development of RKN Resistant Pepper Varieties

For most breeding objectives, commercial breeders work within germplasm that is "cultivated," "cultivated type," or "elite." As used herein, "elite" or "cultivated" variety means a variety that has resulted from breeding and selection for superior horticultural performance for use in agriculture. This germplasm is easier to breed because it generally performs well when evaluated for horticultural performance. A number of cultivated pepper types have been developed, which are agronomically elite and appropriate for commercial cultivation. However, the performance advantage a cultivated germplasm provides can be offset by a lack of allelic diversity. Breeders generally accept this tradeoff because progress is faster when working with cultivated material than when breeding with genetically diverse sources.

In contrast, when cultivated germplasm is crossed with non-cultivated germplasm, a breeder can gain access to novel alleles from the non-cultivated type. However, this approach generally presents significant difficulties due to fertility problems associated with crosses between diverse lines, and negative linkage drag from the non-cultivated parent. For example, non-cultivated pepper lines can provide alleles associated with pest resistance. However, these non-cultivated lines may have poor horticultural qualities such as undesirable fruit shape, undesirable immature fruit color, small fruit size, or low yield.

The process of introgressing desirable resistance genes from non-cultivated lines into elite cultivated lines while avoiding problems with linkage drag or low heritability of the desired trait in crosses with the non-cultivated lines is a long and often arduous process. Success in deploying alleles derived from wild relatives therefore strongly depends on minimal or truncated introgressions that lack detrimental effects and reliable marker assays that replace phenotypic screens. Success is further defined by simplifying genetics for key attributes to allow focus on genetic gain for quantitative traits such as pest resistance. Moreover, the process of introgressing genomic regions from non-cultivated lines can be greatly facilitated by the availability of accurate markers for marker-assisted selection (MAS).

One of skill in the art would therefore understand that the alleles, polymorphisms, and markers provided by the invention allow the tracking and introduction of any of the genomic regions identified herein into any genetic background. In addition, the genomic regions associated with pest resistance disclosed herein can be introgressed from one genotype to another and tracked using MAS. Thus, the novel, accurate markers associated with pest resistance provided herein will facilitate the development of pepper plants having beneficial phenotypes. For example, seed can be genotyped using the markers of the present invention in order to select for plants comprising desired genomic regions associated with pest resistance, without the need for growing plants to maturity to evaluate the phenotype. Moreover, MAS allows identification of plants homozygous or heterozygous for a desired introgression.

Phenotypic evaluation of large plant populations is time-consuming, resource-intensive and not reproducible in every environment. Marker-assisted selection offers a feasible alternative. Molecular assays designed to detect unique polymorphisms, such as SNPs, are versatile. However, they may fail to discriminate alleles within and among pepper species in a single assay. Structural rearrangements of chromosomes such as deletions impair hybridization and extension of synthetically labeled oligonucleotides. In the case of duplication events, multiple copies are amplified in a single reaction without distinction. The development and validation of accurate and highly predictive markers are therefore essential for successful MAS breeding programs.

In certain embodiments, the genomic regions identified herein may be introgressed from any *Capsicum annuum* type into any *Capsicum annuum* type. Types of *Capsicum annuum* include, but are not limited to Anaheim, Ancho/Poblano, Asian long slim, Asian short, Blocky or Bell, Capia, Cascabel, Cayenne, Chiltepins or Small Hots, Corno di Toro, Cubanelle, 'Fresno Chili', Jalapeno, Ornamental, Pasilla, Pimiento, Santa Fe Grande, Serrano, and Waxy peppers, including Hungarian wax/Banana/Hungarian white.

In certain embodiments, the identified genomic regions are introduced from jalapeno type pepper into a non-jalapeno variety. Pepper fruit shapes are well-known to those skilled in the art of pepper breeding. Jalapeno peppers are a type of *Capsicum annuum* that have a characteristic fruit shape. Jalapeno fruits are typically bullet-shaped and have a length to width ratio of about 2.5 to 1 (FIG. 1). For example, a fruit having a length of about 10 cm would be expected to be about 4 cm wide. The fruit typically has thick walls of about 5-6 mm and the dry matter content is normally around 7%. The fruit of most plants develops from a medium green at the immature stage to red at the mature stage. As a commercial product, the fruits are harvested at the green stage. The pungency of jalapeno peppers varies from 0 units to over 5000 units on the Scoville scale.

Figure 2:
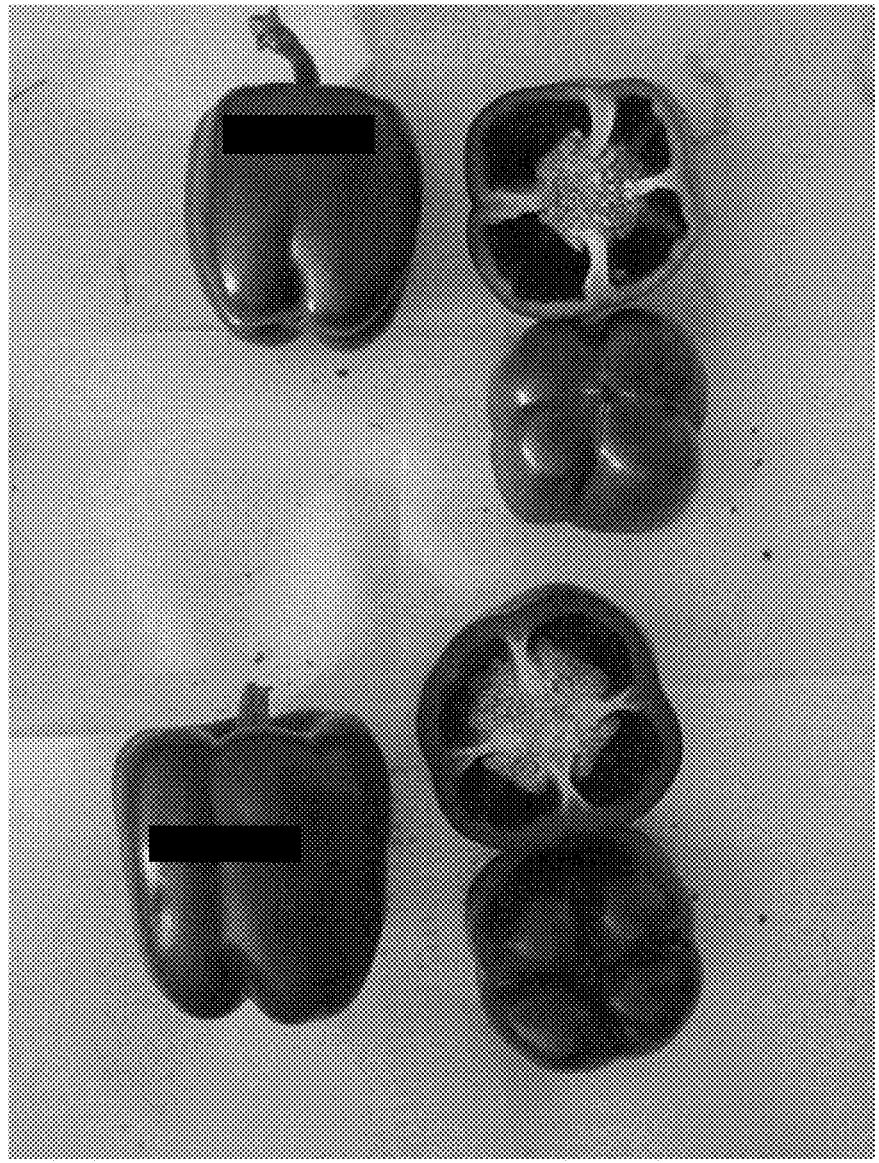
FIG. 2: Fruit of blocky peppers are generally characterized by a length to width ratio of 0.8 to 1.2, while in some regions this ratio can be between 0.8 and 1.4. Colors of the fruit can vary. The most common colors are white, purple, and green at the immature stage, and red, yellow, green, orange, and brown at the mature fruit stage

Non-jalapeno varieties include blocky type peppers, half long-type peppers, and ¾ long-type peppers. In certain examples, non-jalapeno varieties include, but are not limited to Anaheim, Ancho/Poblano, Asian Long Slim, Asian Short, Blocky or Bell, Capia, Cascabel, Cayenne, Chiltepins or Small Hots, Corno di Toro, Cubanelle, 'Fresno Chili', Hungarian Wax/Banana/Hungarian White, Ornamental, Pasilla, Pimiento, Santa Fe Grande, Serrano, and Waxy peppers. Non-jalapeno varieties produce fruit with a length to width ratio of less than about 2.0 to 1, for example less than about 1.2. Non-jalapeno varieties include pepper plants producing fruit with a length to width ratio from 0.8 to 1.2. As used herein, blocky type pepper refers to a pepper wherein the length of the fruit is about the same as the width of the fruit. For example, the length of the fruit is about 0.8, about 0.9, about 1.0, about 1.1, or less than 1.2 of the width of the fruit (FIG. 2). As used herein, half long type pepper refers to a pepper wherein the length of the fruit is about 1.2 to about 1.5 of the width of the fruit. As used herein, ¾ long type pepper, often known as lamuyo refers to a pepper wherein the length of the fruit is more than about 1.5 of the width of the fruit. These peppers can have a variety of different colors, for example white, purple, and green at the immature stage, and for example red, yellow, green, orange, and brown at the mature fruit stage. It is also well-known that definitions vary regionally. For example, in the United States peppers with a length to with ratio of 1.2 to 1.4 are often referred to as "deep blocky", while the terms half long and lamuyo are used interchangeably for sweet peppers with a length to width ratio over 1.4.

Many desirable traits that are successfully introduced through introgression can also be introduced directly into a plant by the use of molecular techniques. One aspect of the invention includes plants with a genome that has been changed by any method using site-specific genome modification techniques. Techniques of site-specific genome modification include the use of enzymes such as, endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp 1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

Another aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit resistance to RKN. Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a pre-determined site by methods of site-directed integration. Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

IV. Molecular Assisted Breeding Techniques

Genetic markers that can be used in the practice of the present invention include, but are not limited to, restriction fragment length polymorphisms (RFLPs), amplified fragment length polymorphisms (AFLPs), simple sequence repeats (SSRs), simple sequence length polymorphisms (SSLPs), single nucleotide polymorphisms (SNPs), insertion/deletion polymorphisms (Indels), variable number tandem repeats (VNTRs), and random amplified polymorphic DNA (RAPD), isozymes, and other markers known to those skilled in the art. Marker discovery and development in crop plants provides the initial framework for applications to marker-assisted breeding activities (U.S. Patent Pub. Nos.: 2005/0204780, 2005/0216545, 2005/0218305, and 2006/00504538). The resulting "genetic map" is the representation of the relative position of characterized loci (polymorphic nucleic acid markers or any other locus for which alleles can be identified) to each other.

Polymorphisms comprising as little as a single nucleotide change can be assayed in a number of ways. For example, detection can be made by electrophoretic techniques including a single strand conformational polymorphism (Orita et al. (1989) *Genomics,* 8(2), 271-278), denaturing gradient gel electrophoresis (Myers (1985) *EPO* 0273085), or cleavage fragment length polymorphisms (Life Technologies, Inc., Gathersberg, Md.), but the widespread availability of DNA sequencing often makes it easier to simply sequence amplified products directly. Once the polymorphic sequence difference is known, rapid assays can be designed for progeny testing, typically involving some version of PCR amplification of specific alleles (PASA; Sommer, et al. (1992) *Biotechniques* 12(1), 82-87), or PCR amplification of multiple specific alleles (PAMSA; Dutton and Sommer (1991) *Biotechniques,* 11(6), 700-7002).

Polymorphic markers serve as useful tools for assaying plants for determining the degree of identity of lines or varieties (U.S. Pat. No. 6,207,367). These markers form the basis for determining associations with phenotypes and can be used to drive genetic gain. In certain embodiments of methods of the invention, polymorphic nucleic acids can be used to detect in a pepper plant a genotype associated with pest resistance, identify a pepper plant with a genotype associated with pest resistance, and to select a pepper plant with a genotype associated with pest resistance. In certain embodiments of methods of the invention, polymorphic nucleic acids can be used to produce a pepper plant that comprises in its genome an introgressed locus associated with pest resistance. In certain embodiments of the invention, polymorphic nucleic acids can be used to breed progeny pepper plants comprising a locus or loci associated with pest resistance.

Genetic markers may include "dominant" or "codominant" markers. "Codominant" markers reveal the presence of two or more alleles (two per diploid individual). "Dominant" markers reveal the presence of only a single allele. Markers are preferably inherited in codominant fashion so that the presence of both alleles at a diploid locus, or multiple alleles in triploid or tetraploid loci, are readily detectable, and they are free of environmental variation, i.e., their heritability is 1. A marker genotype typically comprises two marker alleles at each locus in a diploid organism. The marker allelic composition of each locus can be either homozygous or heterozygous. Homozygosity is a condition where both alleles at a locus are characterized by the same nucleotide sequence. Heterozygosity refers to different conditions of the allele at a locus.

Nucleic acid-based analyses for determining the presence or absence of the genetic polymorphism (i.e. for genotyping) can be used in breeding programs for identification, selection, introgression, and the like. A wide variety of genetic markers for the analysis of genetic polymorphisms are available and known to those of skill in the art. The analysis may be used to select for genes, portions of genes, QTL, alleles, or genomic regions that comprise or are linked to a genetic marker that is linked to or associated with pest resistance in pepper plants.

As used herein, nucleic acid analysis methods include, but are not limited to, PCR-based detection methods (for example, TaqMan assays), microarray methods, mass spectrometry-based methods and/or nucleic acid sequencing methods, including whole genome sequencing. In certain embodiments, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

One method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. Nos. 4,683,202; 4,582,788; and 4,683,194), using primer pairs that are capable of hybridizing to the proximal sequences that define a polymorphism in its double-stranded form. Methods for typing DNA based on mass spectrometry can also be used. Such methods are disclosed in U.S. Pat. Nos. 6,613,509 and 6,503,710, and references found therein.

Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entirety. However, the compositions and methods of the present invention can be used in conjunction with any polymorphism typing method to type polymorphisms in genomic DNA samples. These genomic DNA samples used include but are not limited to, genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods, for example as disclosed in U.S. Pat. No. 5,800,944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., *Genome Res.* 13:513-523 (2003); Cui et al., *Bioinformatics* 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening of a plurality of polymorphisms. Typing of target sequences by microarray-based methods is disclosed in U.S. Pat. Nos. 6,799,122; 6,913,879; and 6,996,476.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR, forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5' 4 3' exonuclease activity cleaves the probe and separates the reporter dye from the quencher dye resulting in increased fluorescence of the reporter.

In another embodiment, a locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays.

V. Definitions

The following definitions are provided to better define the present invention and to guide those of ordinary skill in the art in the practice of the present invention. Unless otherwise noted, terms are to be understood according to conventional usage by those of ordinary skill in the relevant art.

As used herein, the term "plant" includes plant cells, plant protoplasts, plant cells of tissue culture from which pepper plants can be regenerated, plant calli, plant clumps and plant cells that are intact in plants or parts of plants such as pollen, flowers, seeds, leaves, stems, and the like.

As used herein, the term "population" means a genetically heterogeneous collection of plants that share a common parental derivation.

As used herein, the terms "variety" and "cultivar" mean a group of similar plants that by their genetic pedigrees and performance can be identified from other varieties within the same species.

As used herein, an "allele" refers to one of two or more alternative forms of a genomic sequence at a given locus on a chromosome.

A "quantitative trait locus" (QTL) is a chromosomal location that encodes for at least a first allele that affects the expressivity of a phenotype.

As used herein, a "marker" means a detectable characteristic that can be used to discriminate between organisms. Examples of such characteristics include, but are not limited to, genetic markers, biochemical markers, metabolites, morphological characteristics, and agronomic characteristics.

As used herein, the term "phenotype" means the detectable characteristics of a cell or organism that can be influenced by gene expression.

As used herein, the term "genotype" means the specific allelic makeup of a plant.

As used herein, "elite" or "cultivated" variety means any variety that has resulted from breeding and selection for superior agronomic performance. An "elite plant" refers to a plant belonging to an elite variety. Numerous elite varieties are available and known to those of skill in the art of pepper breeding. An "elite population" is an assortment of elite individuals or varieties that can be used to represent the state of the art in terms of agronomically superior genotypes of a given crop species, such as pepper. Similarly, an "elite germplasm" or elite strain of germplasm is an agronomically superior germplasm.

As used herein, the term "introgressed" or "introgression," when used in reference to a genetic locus, refers to a genetic locus that has been introduced into a new genetic background, such as through backcrossing. Introgression of a genetic locus can be achieved through plant breeding methods and/or by molecular genetic methods. Such molecular genetic methods include, but are not limited to, various plant transformation techniques and/or methods that provide for homologous recombination, non-homologous recombination, site-specific recombination, and/or genomic modifications that provide for locus substitution or locus conversion.

As used herein, the term "linked" or "genetically linked," when used in the context of nucleic acid markers and/or genomic regions, means that the markers and/or genomic regions are located in proximity on the same linkage group or chromosome such that they tend to segregate together at meiosis.

As used herein, "resistance locus" means a locus associated with resistance or tolerance to a pest. For instance, a resistance locus according to the present invention may, in one embodiment, control resistance or susceptibility to RKN.

As used herein, "resistance allele" means the nucleic acid sequence associated with resistance or tolerance to a pest.

As used herein, "resistance" or "improved resistance" in a plant to pests is an indication that the plant is more able to reduce pest damage than a non-resistant or less-resistant plant. One of skill will appreciate that plant resistance to pests varies widely, and can represent a spectrum of more-resistant or less-resistant phenotypes. However, by simple observation, one of skill can generally determine the relative resistance of different plants, plant varieties, or plant families to pests, and furthermore, will also recognize the phenotypic gradations of "resistance."

The term "about" is used to indicate that a value includes the standard deviation of error for the device or method being employed to determine the value. The use of the term "or" in the claims is used to mean "and/or" unless explicitly indicated to refer to alternatives only or the alternatives are mutually exclusive, although the disclosure supports a definition that refers to only alternatives and to "and/or." When used in conjunction with the word "comprising" or other open language in the claims, the words "a" and "an" denote "one or more," unless specifically noted. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

EXAMPLES

Example 1. Identification of a Resistance Source

A jalapeno pepper inbred line, HJA-114-1011, was identified in a screen as a source of resistance to *M. enterolobii*, *M. incognita*, *M. javanica*, and *M. arenaria*. HJA-114-1011 is a plant selection from the open pollinated variety 'Ole'.

Example 2. Genotyping of Resistant Plants

Figure 3:
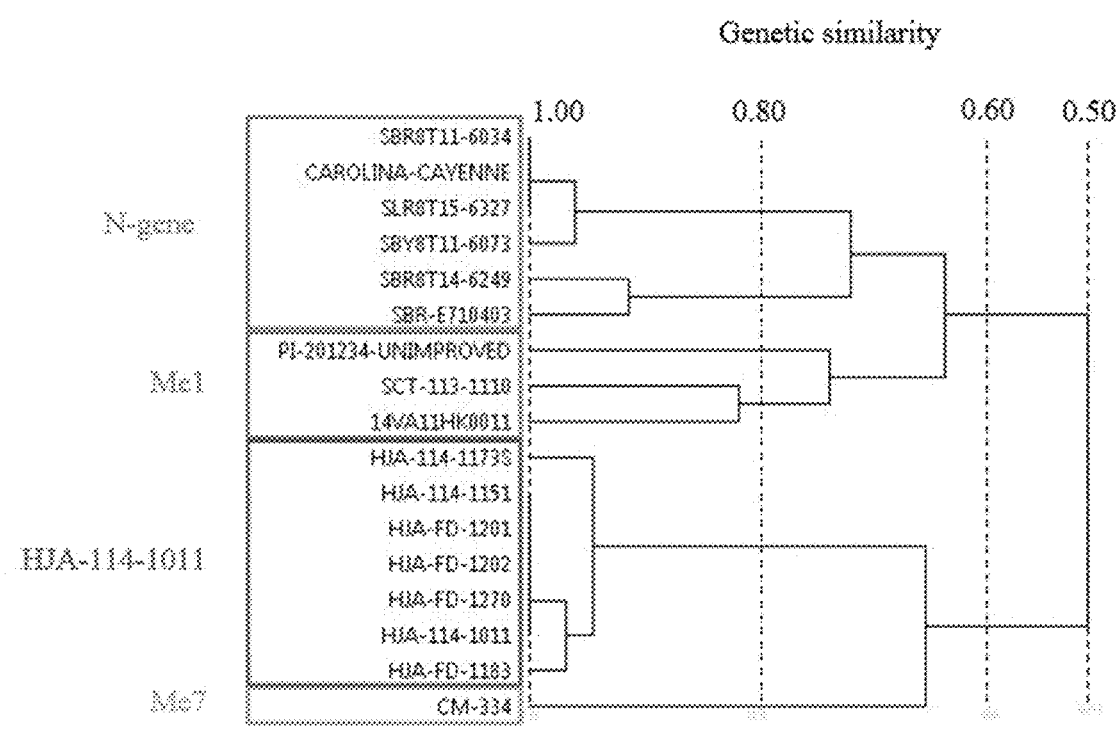
FIG. 3: Genotype analysis of the nematode resistance region on chromosome 9.

To determine if the resistance of HJA-114-1011 is distinct from any of the known resistance sources, a genetic similarity analysis was performed. SNP markers in the nematode resistance region of chromosome 9 were identified and used to determine the genotype of HJA-114-1011. Clustering analysis based on genetic similarity was used to compare the genotype of HJA-114-1011 to several inbred lines and resistance sources with known resistance genes (FIG. 3). It was found that all lines comprising HJA-114-1011 resistance were clustered in a distinct group from lines comprising resistance from other sources. This analysis indicated that the haplotype shared by HJA-114-1011 and its derivatives in this genomic region is highly unrelated (genetic similarity of 50%) to haplotypes associated with Me1 and N-gene sources. No shared haplotype could be identified between HJA-114-1011 and the Me1 donor within the nematode gene cluster on chromosome 9. This suggests that RKN resistance from HJA-144-1011 is not related to Me1. In fact, each resistance gene formed its own cluster in the phylogenetic tree and is thus highly genetically distinct from the other resistance genes. This demonstrates that the HJA-114-1011 nematode resistance locus is unique and unrelated to the N-gene, Me1, and Me7 resistance loci.

Example 3. QTL Mapping

A recombinant inbred line (RIL) population from a cross between HJA-114-1096 (nematode sensitive) and HJA-114-1011 (nematode resistant) was utilized to map the QTL locus conferring resistance to *M. enterolobii* from HJA-114-1011. 150 individuals from this RIL population were screened in a controlled bioassay using a pure *M. enterolobii* isolate. The bioassay consists of the tester lines, positive and negative controls. The resistant parent (HJA-114-1011) was used as a positive control, and the sensitive parent (HJA-114-1096) was used as a negative control. Other negative controls were, for example, Carolina Cayenne, Spartacus or GCW. Two-week-old seedlings were inoculated with 500 nematodes per plant by pipetting a 1 mL of a homogeneous nematode suspension (500 nematodes/mL) into an approximately 3 cm deep hole at the base of the plant. Preferably fresh inoculum is used, but inoculum that has been stored at 4° C. for one day can also be used in this bioassay. Plants were subsequently maintained between 18° C. and 25° C., with the optimal temperature of 22° C. Excessive watering was avoided for the first 3 days to ensure that the nematodes would not wash away. The bioassay screen had 3 replicates of 10 plants per line and all galls were counted for each plant six weeks post inoculation. These counts were used to calculate the LS mean for each line, which was used in the subsequent QTL analysis.

The same RIL individuals were genotyped using TaqMan markers spaced across the genome which were polymorphic between the parental lines. The combination of genome wide genotypes and gall count phenotypes were used to QTL map nematode resistance coming from HJA-114-1011. One major effect QTL was found on chromosome 9 located between 100-122 cM and explains 64.4% of the phenotypic variation. The 2-LOD interval was positioned at 110.3-113.7 cM, while the 1-LOD interval was similar and localized at 110.4-113 cM.

Figure 5:
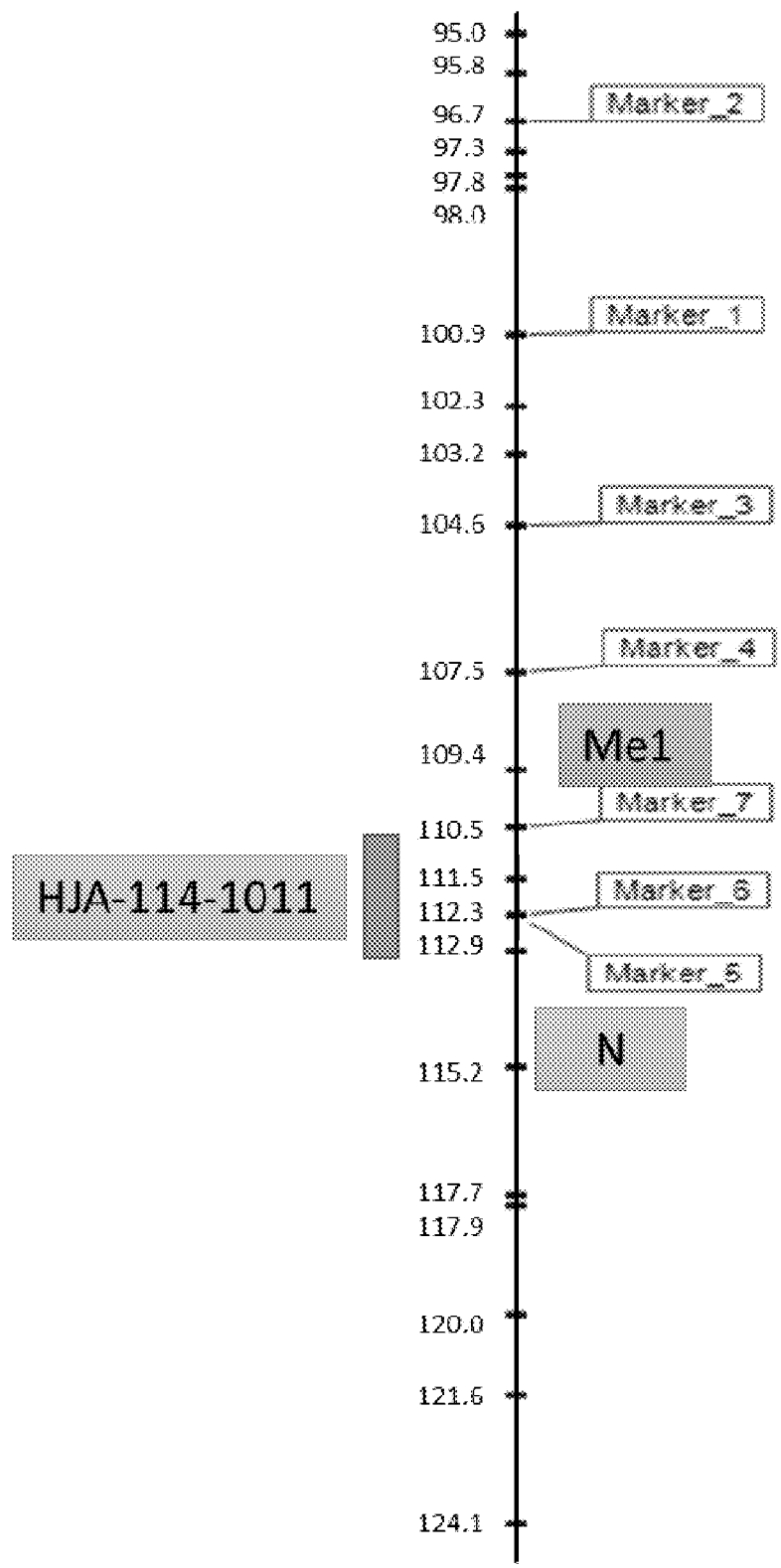
FIG. 5: Genetic map of the nematode resistance region on chromosome 5 showing marker positions and the position of the N-locus, Me1, and the HJA-114-1011 locus.

To fine map the chromosome 9 QTL, haplotypes of the 100-122 cM region on chromosome 9 were identified within the RIL population (FIG. 4). Fourteen different haplotypes were found with varying numbers of RIL individuals contributing to each haplotype. The LS means for gall count were calculated across each haplotype group (FIG. 4). Based on this analysis the region conferring resistance from HJA-114-1011 was determined to be between 109-114 cM, which approximately correlates to 110-112 cM on the consensus map. Marker_7, Marker_8, and Marker_9 can thus be used to select for the resistance locus of HJA-114-1011 (Table 1). Adding this region to the genetic map of chromosome 9 region, shows that the HJA-114-1011 region does not overlap with well-known resistance loci N and Me1 (FIG. 5).

TABLE 1

Markers associated with the resistance locus of HJA-114-1011.

| | Public SNP position CM334 v.1.55 | Marker Sequence (SEQ ID NO.) | SNP Position | Allele | Forward Primer (SEQ ID NO.) | Reverse Primer (SEQ ID NO.) | Probe 1 (SEQ ID NO.) | Probe 2 (SEQ ID NO.) |
|---|---|---|---|---|---|---|---|---|
| Marker_6 | | 1 | 111 | C/A | 2 | 3 | 4 | 5 |
| Marker_7 | 250,504,749 | 6 | 130 | T/A | 7 | 8 | 9 | 10 |
| Marker_8 | 25,0338,645 | 11 | 151 | A/G | 12 | 13 | 14 | 15 |
| Marker_9 | 250,502,864 | 16 | 151 | T/C | 17 | 18 | 19 | 20 |
| Marker_10 | 241570991 | 21 | 151 | G/C | 22 | 23 | 24 | 25 |

Example 4. Sequence Analysis

Sequence analysis was conducted to evaluate how many single nucleotide polymorphisms (SNPs) are unique HJA-114-1011 on chromosome 9. The sequence capture data of twenty-five elite inbred jalapeno lines and 219 lines from other germplasm types was analyzed against HJA-114-1011. Two lines in the jalapeno group were derived from HJA-114-1011 and were grouped with HJA-114-1011 for this analysis. The analysis consisted of calculating the allele frequency for each SNP within the two groups: HJA-114-1011 derived, and non-derived jalapenos. When looking across the chromosome, there is a significant increase of number of unique SNPs to HJA-114-1011 in the QTL region. In total, 41 SNPs were found to be unique to HJA-114-1011 in a 560 kb region co-localized to the QTL region. Methods developed to detect these unique SNPs can be used to track the HJA-114-1011 nematode resistance trait within all types of pepper germplasm.

The invention claimed is:

1. A method for producing a *Capsicum annuum* plant exhibiting resistance to root knot nematodes, comprising:
   a) crossing a *Capsicum annuum* plant comprising an introgressed allele on chromosome 9 that confers increased resistance to root knot nematodes compared to a plant not comprising said allele, wherein said plant is a non-jalapeno variety, and wherein said introgressed allele is located between Marker_6 (SEQ ID NO: 1) and Marker_10 (SEQ ID NO: 21) on chromosome 9 with itself or with a second *Capsicum annuum* plant of a different genotype to produce one or more progeny plants; and
   b) selecting a progeny plant comprising said introgressed allele.

2. The method of claim 1, wherein selecting said progeny plant comprises identifying a genetic marker genetically linked to said introgressed allele.

3. The method of claim 2, wherein selecting said progeny plant comprises identifying a genetic marker within or genetically linked to a genomic region between 250,338,645 bp and 250,504,749 bp on chromosome 9 on the physical map of CM334 v1.55.

4. The method of claim 3, wherein selecting said progeny plant comprises identifying a genetic marker within or genetically linked to a genomic region flanked in the genome of said plant by marker locus Marker_7 (SEQ ID NO: 6) and marker locus Marker_9 (SEQ ID NO: 16).

5. The method of claim 4, wherein selecting a progeny plant comprises detecting at least one polymorphism at a locus selected from the group consisting of marker locus Marker_7 (SEQ ID NO: 6), marker locus Marker_8 (SEQ ID NO: 11), and marker locus Marker_9 (SEQ ID NO: 16).

6. The method of claim 1, wherein said progeny plant is an $F_2$-$F_6$ progeny plant.

7. The method of claim 1, wherein producing said progeny plant comprises backcrossing.

8. The method of claim 7, wherein backcrossing comprises from 2-7 generations of backcrossing.

9. A method of producing a *Capsicum annuum* plant exhibiting resistance to root knot nematodes, comprising introgressing into a plant a root knot nematode resistance allele, wherein said resistance allele is defined as located in a genomic region between 250,338,645 bp and 250,504,749 bp on chromosome 9 on the physical map of CM334 v1.55.

10. The method of claim 9, wherein said genomic region is flanked by Marker_7 (SEQ ID NO: 6) and marker locus Marker_9 (SEQ ID NO: 16).

11. The method of claim 9, wherein said introgressing comprises backcrossing.

12. The method of claim 9, wherein said introgressing comprises marker-assisted selection.

13. The method of claim 9, wherein said introgressing comprises assaying for said root knot nematode resistance.

14. A method of selecting a *Capsicum annuum* plant exhibiting resistance to root knot nematodes, comprising:
   a) crossing a *Capsicum annuum* plant comprising an introgressed allele on chromosome 9 that confers increased resistance to root knot nematodes compared to a plant not comprising said allele, wherein said plant is a non-jalapeno variety, and wherein said introgressed allele is located between Marker_6 (SEQ ID NO: 1) and Marker_10 (SEQ ID NO: 21) on chromosome 9 with itself or with a second *Capsicum annuum* plant of a different genotype to produce one or more progeny plants; and
   b) selecting a progeny plant comprising said introgressed allele.

15. The method of claim 14, wherein selecting said progeny plant comprises identifying a genetic marker genetically linked to said introgressed allele.

16. The method of claim 14, wherein selecting said progeny plant comprises identifying a genetic marker within or genetically linked to a genomic region between 250,338,645 bp and 250,504,749 bp on chromosome 9 on the physical map of CM334 v1.55.

17. The method of claim 14, wherein selecting said progeny plant comprises identifying a genetic marker within or genetically linked to a genomic region flanked in the genome of said plant by marker locus Marker_7 (SEQ ID NO: 6) and marker locus Marker_9 (SEQ ID NO: 16).

18. The method of claim 16, wherein selecting a progeny plant comprises detecting at least one polymorphism at a locus selected from the group consisting of marker locus Marker_7 (SEQ ID NO: 6), marker locus Marker_8 (SEQ ID NO: 11), and marker locus Marker_9 (SEQ ID NO: 16).

19. The method of claim 14, wherein said progeny plant is an $F_2$-$F_6$ progeny plant.

20. The method of claim 14, wherein producing said progeny plant comprises backcrossing.

21. The method of claim 20, wherein backcrossing comprises from 2-7 generations of backcrossing.

* * * * *